United States Patent

Bailey

(10) Patent No.: US 9,107,810 B2
(45) Date of Patent: Aug. 18, 2015

(54) GASTRIC PORT SYSTEM

(75) Inventor: F. Kristen Bailey, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1207 days.

(21) Appl. No.: 12/145,148

(22) Filed: Jun. 24, 2008

(65) Prior Publication Data

US 2009/0318854 A1    Dec. 24, 2009

(51) Int. Cl.
*A61J 15/00*    (2006.01)
*A61M 39/02*    (2006.01)

(52) U.S. Cl.
CPC .......... *A61J 15/0034* (2013.01); *A61J 15/0038* (2013.01); *A61J 15/0053* (2013.01); *A61J 15/0061* (2013.01); *A61M 39/0247* (2013.01); *A61J 15/0015* (2013.01); *A61M 2039/0255* (2013.01); *A61M 2210/1053* (2013.01)

(58) Field of Classification Search
CPC ............ A61F 5/0003; A61F 2002/045; A61F 5/0063; A61F 5/0066; A61F 5/0083; A61F 5/0069; A61F 2/0018; A61M 16/0415; A61M 2210/1053; A61M 25/0127; A61N 1/375; A61J 15/00; A61J 15/0061; A61J 15/0038; A61J 15/0034
USPC ................................................. 604/175, 539
See application file for complete search history.

(56) References Cited

U.S. PATENT DOCUMENTS

| | | | |
|---|---|---|---|
| 3,253,594 A * | 5/1966 | Matthews et al. ........ | 604/103.03 |
| 3,565,073 A | 2/1971 | Geisy | |
| 3,952,726 A | 4/1976 | Hennig et al. | |
| 4,205,678 A | 6/1980 | Adair | |
| 4,338,937 A | 7/1982 | Lerman | |
| 4,784,646 A | 11/1988 | Feingold | |
| 5,484,420 A | 1/1996 | Russo | |
| 5,507,303 A | 4/1996 | Kuzma | |
| 5,624,410 A | 4/1997 | Tsukada et al. | |
| 5,690,656 A | 11/1997 | Cope et al. | |
| 5,720,734 A | 2/1998 | Copenhaver et al. | |
| 5,817,067 A | 10/1998 | Tsukada | |
| 6,039,714 A * | 3/2000 | Cracauer et al. ............. | 604/174 |
| 6,126,647 A | 10/2000 | Posey et al. | |
| 6,719,768 B1 * | 4/2004 | Cole et al. ..................... | 606/153 |
| 7,211,094 B2 | 5/2007 | Gannoe et al. | |
| 7,255,682 B1 | 8/2007 | Bartol, Jr. et al. | |
| 2004/0088008 A1 * | 5/2004 | Gannoe et al. .................... | 607/1 |
| 2005/0096750 A1 | 5/2005 | Kagan et al. | |
| 2005/0165432 A1 * | 7/2005 | Heinrich ....................... | 606/167 |
| 2006/0079845 A1 * | 4/2006 | Howard et al. ............... | 604/175 |
| 2006/0195139 A1 | 8/2006 | Gertner | |
| 2006/0247678 A1 | 11/2006 | Weisenburgh, II et al. | |
| 2007/0142780 A1 * | 6/2007 | Van Lue ................... | 604/167.01 |
| 2007/0156117 A1 | 7/2007 | Adams et al. | |

* cited by examiner

*Primary Examiner* — Andrew Gilbert
*Assistant Examiner* — Matthew A Engel
(74) *Attorney, Agent, or Firm* — Brinks Gilson & Lione (57) ABSTRACT

A gastric port system for transport of materials to the interior of a body cavity that may include a port configured to be disposed between a first body cavity and an area adjacent to the first body cavity. The gastric port system may further include a first bolster disposed on the port where the first bolster includes a magnet, and a second bolster disposed on the port where the second bolster includes a magnet, and the magnets are attracted to each other.

13 Claims, 6 Drawing Sheets

GASTRIC PORT SYSTEM

BACKGROUND

The present system relates to medical devices, and more particularly, to gastric port systems for delivery of materials to the interior of a body cavity.

Patients for which normal ingestion of food becomes difficult or impossible may require placement of a feeding tube to assist in providing their nutritional needs. For some individuals, such as comatose patients, stroke victims, or those with a compromised gastrointestinal tract and the like, this may require placement of a tube that is introduced percutaneously into the stomach for delivery of nutritional products directly into the stomach or jejunum. The procedure, known as a Percutaneous Endoscopic Gastrostomy (PEG), involves the introduction of an endoscope into the stomach. The desired site where the stoma is to be created is indicated from above by depressing the abdomen and viewing the depressed site with the endoscope. Transillumination may also be utilized to locate the desired site through the abdominal wall. A sheathed needle or trocar punctures the abdominal wall and enters the stomach, creating a stoma. The needle is removed and a looped insertion wire is introduced through the sheath where it is grasped by a snare or forceps deployed from the working channel of the endoscope. Once it is captured, the insertion wire is pulled into the working channel of the endoscope. The endoscope is then withdrawn from the patient via the oral cavity, pulling the insertion wire with it.

In the standard Ponsky method (or "pull" method), the distal loop of a percutaneous gastrostomy feeding tube is coupled to the insertion wire loop exiting the patient's mouth. With the insertion wire now tethered to the gastrostomy feeding tube, the endoscopist retracts the portion of the insertion wire exiting the stoma, thereby pulling the gastrostomy feeding tube into the patient's mouth and towards the stomach. With continued retraction of the insertion wire, the distal end of the gastrostomy feeding tube is pulled out through the stoma. The gastrostomy feeding tube typically includes a tapered dilator portion to aid its passage through the stoma. Once the feeding tube has been properly positioned with the proximal end cap or bolster of the feeding tube against the internal wall of the stomach, it is secured by an external bolster positioned against the outside of the abdomen wall.

In a variation of the PEG procedure known as the "push" method, the gastrostomy feeding tube is advanced or pushed down the esophagus by the physician and into position in the stomach using a wire guide that has been placed in the same manner as the insertion wire in the "pull" method. More specifically, the feeding tube is loaded on the portion of the wire guide exiting the patient's mouth by passing the end of the wire guide through a lumen extending through the length of the feeding tube. While holding the wire guide stationary, the physician pushes the feeding tube along the wire guide through the patient's mouth, into the stomach, and then out through the stoma. The feeding tube is then secured in the same manner as the "pull" method.

Yet another method is simply to insert the feeding tube through the patient's abdominal wall and bypass insertion through the mouth. However, this method typically requires the attachment of a bolster to the interior portion of the feeding tube, which may need to be delivered and attached endoscopically. Alternatively, when the device has a low profile, it may be inserted using the Seldinger technique.

As stated above, typically, a retention bolster is positioned against the inside and/or outside of the abdomen wall, or whichever body cavity or area the gastric port is being used in relation to. The bolster is present to keep in place and support the gastric port and prevent sudden or unexpected removal of the port from the stoma site. Bolsters for supporting ports, such as feeding tubes, inside or outside the body have generally focused on maintaining the secure anchoring of the device to the patient. To provide support, bolsters have employed flanges, cross-bars, discs, or balloons for contacting the surface of the tissue. In the past, however, bolsters have tended to increase the localized pressure at the exit site, especially when the port, either accidentally or intentionally, is moved thereabout.

One particular application exhibiting the deficiencies of existing bolsters involves the use of PEG tubes to provide long term access to the stomach. A PEG tube is often maintained at its stoma site by an internal and external retention bolster for several months while the PEG tube is used to provide access to the stomach. Existing bolsters, however, remain inflexibly clamped to the feeding tube so as to maintain the catheter in position during use. As a consequence, these bolsters do not accommodate the unavoidable movements of the port during extended periods of time or, for example, the loss or gain of weight of the patient subsequent to introduction of the port.

A need therefore exists for an improved retention bolster for use adjacent to a body surface to support a gastric port.

BRIEF SUMMARY

The foregoing problems are solved and technical advance is achieved with an illustrative gastric port system. The gastric port system for transport of materials to the interior of a body cavity includes a port that is configured to be disposed between a first body cavity and an area adjacent to the first body cavity. The gastric port system includes a first bolster disposed on a first portion of the port and configured to contact a bodily surface of the body cavity. The gastric port system includes a second bolster disposed on a second portion of the port and configured to contact a bodily surface of the area adjacent to the cavity. At least one of the first bolster and the second bolster is slidable relative to the port to allow relative movement between the bolsters. The first and second bolster each may include one or more magnets that are configured so that the magnet on the first bolster is attracted to the magnet on the second bolster. Alternatively, one of the bolsters may be made of material that attracts a magnet.

The first bolster may also include a pocket configured to receive a magnet and the second bolster may include a pocket configured to receive a magnet. In another embodiment, one of the first bolster and the second bolster may be a Malecot shaped bolster having a foldable member and a pocket configured to receive a magnet.

In yet another embodiment, a medical device kit is disclosed. The medical device kit may include a port, a catheter, a first bolster, a second bolster, and at least one array of magnets to be disposed on the first bolster and the second bolster.

These and other advantages, as well as the gastric port system itself, will become apparent in the details of construction and operation as more fully described below. Moreover, it should be appreciated that several aspects of the invention can be used with other types of gastric port systems or medical devices.

DETAILED DESCRIPTION OF THE DRAWINGS AND THE PRESENTLY PREFERRED EMBODIMENTS

For the purposes of promoting an understanding of the principles of the gastric port system, reference will now be made to the embodiments illustrated herein. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

Figure 1:
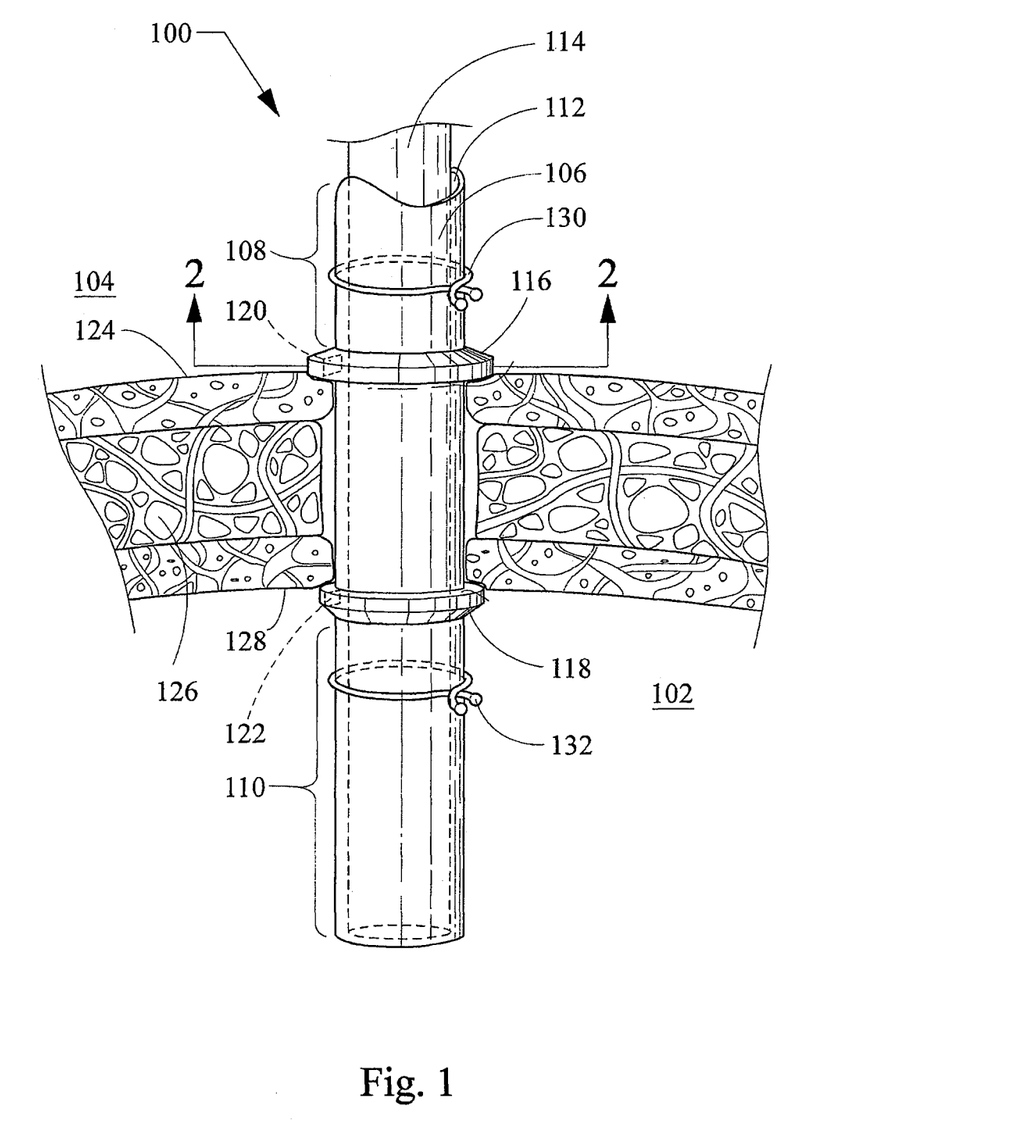
FIG. 1 is an illustration of a gastric port system.

Referring now to FIG. 1, a gastric port system 100 is shown transversing a stoma between a first body cavity 102 and an area 104 adjacent to the first body cavity 102. More specifically, and as illustrated in FIG. 1, the first body cavity 102 may be the abdominal cavity of a patient and area 104 illustrated is an area external to the patient. However, the first body cavity 102 may be any body cavity that would benefit from the advantages disclosed herein. Likewise, area 104 may be a second body cavity adjacent to the first body cavity. For example, the first body cavity 102 may be the abdominal cavity of the patient and the area 104 may be the intestine of the patient.

Gastric port system 100 includes a port 106 that has a proximal portion 108 and a distal portion 110. The proximal portion 108 may be defined as the portion of the port 106 that extends into area 104 and the distal portion 110 may be defined as the portion of the port 106 that extends into first body cavity 102. The port 106 also includes a passageway 112 that allows for the passage of materials through the port 106. More specifically, the passageway 112 allows for the passage of nutritional products or medications directly into the body or body cavity of a patient. Alternatively, a catheter 114 may be introduced to extend through the passageway 112 and may act as the delivery mechanism for materials directly into the body or body cavity of a patient. The port 106 may be made of any material suitable for the placement of the port 106 into a body or body cavity of a patient. Likewise, the catheter 114 may be made of any material suitable for delivery of, for example, nutritional products or medications into the body or body cavity.

A first bolster 116 and a second bolster 118 are shown in FIG. 1. The first bolster 116 may be disposed on the proximal portion 108 of the port 106 and the second bolster 118 may be disposed on the distal portion 110 of the port 106. The first bolster 116 may be slidably disposed on the proximal portion 108 of the port 106. Alternatively, the first bolster 116 may be fixedly attached to the port 106. The first bolster 116 and the second bolster 118 may be different sizes and shapes. For example, the bolsters 116 and 118 may be molded in one piece out of medical grade resilient silicone and the like and may be ring shaped, bowl shaped, T-shaped, Malecot shaped, mushroom-shaped, dome-shaped, conical-shaped, or any other shape that can provide retention for the gastric port system.

The first bolster 116 may contain a magnet 120. The magnet 120 may be on the surface of the bolster 116, such as a bar magnet or any other shaped magnet. Alternatively, the magnet 120 may coat the entire surface area of the bolster 116. The magnet 120 has a particular magnetic strength. As one skilled in the art will appreciate, the magnetic strength of magnet 120 may be chosen to provide a suitable magnetic strength needed for a particular application, such as the varying thickness of an abdominal wall and the sensitivity of bodily tissue to trauma. Further, the bolster 116 may contain more than one magnet 120, variously arranged on the surface of bolster 116. If there is more than one magnet 120, the magnets may have the same or different magnetic strengths, depending on the particular application.

The second bolster 118 contains a magnet 122. The magnet 122 may be on the surface of the bolster 118, or may be embedded within the bolster 118. The magnet 122 may have a surface shape smaller than the surface area of the bolster 118, such as a bar magnet or any other shaped magnet. Alternatively, the magnet 122 may coat the entire surface area of the bolster 118. The magnet 122 has a particular magnetic strength. As one skilled in the art will appreciate, the magnetic strength of magnet 122 may be chosen to maximize the magnetic strength needed for a particular application. Further, the bolster 118 may contain more than one magnet 122, variously arranged on the surface of bolster 118. If there is more than one magnet 122, the magnets may have the same or different magnetic strengths, depending on the particular application, such as the varying thickness of an abdominal wall. The magnet 120 of the first bolster 116 is designed to be attracted to the magnet 122 of the second bolster. In an alternative embodiment, one of the bolsters 116 and 118 may be made of material which is attracted to magnetic material, such as a metallic material.

Figure 2:
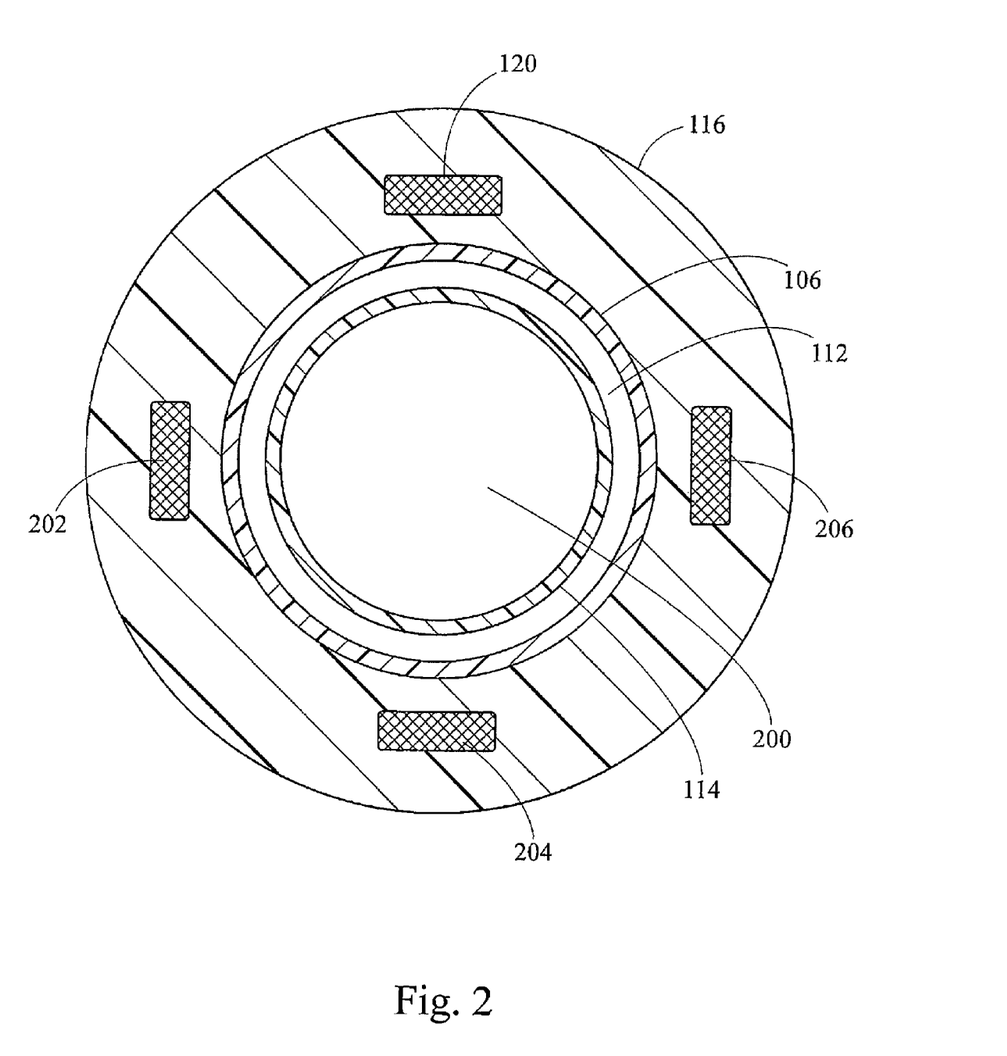
FIG. 2 is an illustration of a retention bolster taken along line 2-2 of FIG. 1.

FIG. 2, taken along line 2-2 in FIG. 1, illustrates the coaxial relationship between the first bolster 116, the port 106, the passageway 112, and the catheter 114. Additionally, FIG. 2 illustrates a lumen 200 extending through the catheter 114 through which nutritional products, medication and the like may flow. While FIG. 2 shows a coaxial relationship between the various components of the gastric port system 100, it should be understood that a coaxial relationship between the components is not necessary, and may be modified to suit a particular application as will be appreciated by one skilled in the art. FIG. 2 shows magnet 120, as well as three additional magnets 202, 204, and 206 respectively, disposed about the circumference of the bolster 116. As one skilled in the art will appreciate, the port system 100 disclosed herein is not limited to a particular number of magnets. Indeed, more or less than four magnets may be used, and may be arranged on the surface of the bolster 116 in varying patterns, depending on the application. Moreover, while FIG. 2 illustrates the coaxial relationship of the first bolster 116 with other components of the port system 100, it should be understood that bolster 118 may have the same or similar relationship relative to the port 106 and the catheter 114. Further, as is described below, second bolster 118 may also have a magnet or magnets, arranged similarly as those described above.

FIG. 1 illustrates the first bolster 116 engaging the first side 124 of a bodily wall 126. The bodily wall 126 may be the material or space between body cavity 102 and area 104. The second bolster 118 is also shown engaging a second side 128 of the bodily wall 126. As will be explained in greater detail below, one or both the first bolster 116 and the second bolster 118 may be slidable relative to the port 106 such that the distance between the first bolster 116 and the second bolster 118 may be adjustable to compensate for or adjust to the thickness of the bodily wall 126.

In an embodiment where the first bolster 116 is slidable relative to the proximal portion 108 of the port 106, a first retaining mechanism 130 may be included. The first retaining mechanism 130 may limit axial movement of the first bolster 116 relative to the proximal portion 108 of the port 106. In an embodiment where the second bolster 118 is slidable relative to the distal portion 110 of the port 106, a second retaining mechanism 132 may be included. The second retaining mechanism 132 may limit axial movement of the second bolster 118 relative to the distal portion 110 of the port 106. The first retaining mechanism 130 and the second retaining mechanism 132 may be a removable plastic twist lock, which is closed about the port 106 to apply a gripping pressure on the port 106 and to prevent axial movement of the bolsters 116 and 118. The retaining mechanisms 130 and 132 may be removed or moved axially along the port 106 to adjust the axial movement range of the bolsters 116 and 118. Alternatively, the retaining mechanisms 130 and 132 may be barbs (not shown) that protrude from the proximal portion 108 and the distal portion 110 of port 106, respectively, and engage the bolsters 116 and 118. The retaining mechanisms 130 and 132 prevent the port 106 from being removed from the bolsters 116 and 118.

Figure 3:
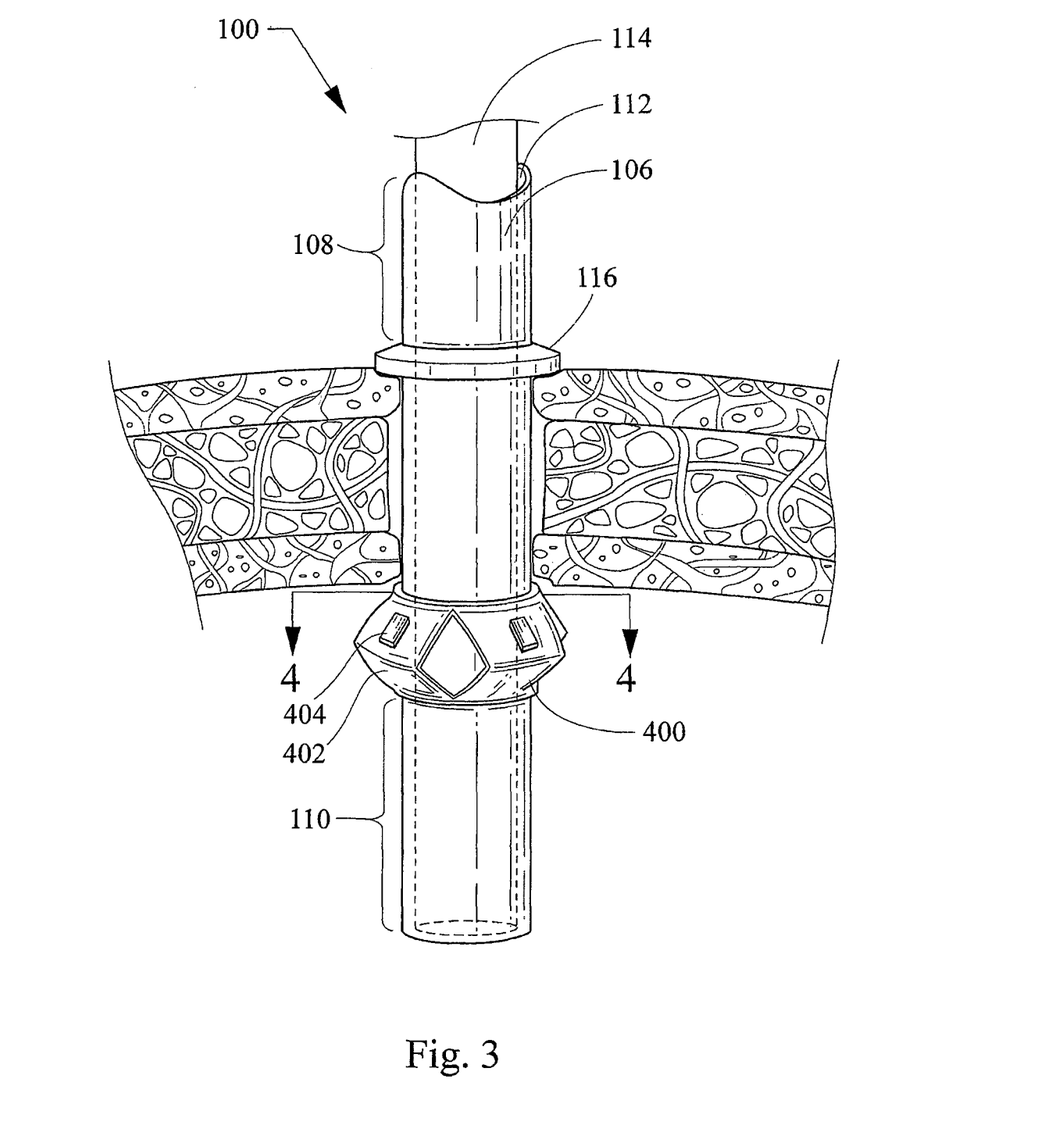
FIG. 3 is an illustration of another embodiment of a gastric port system.
Figure 4:
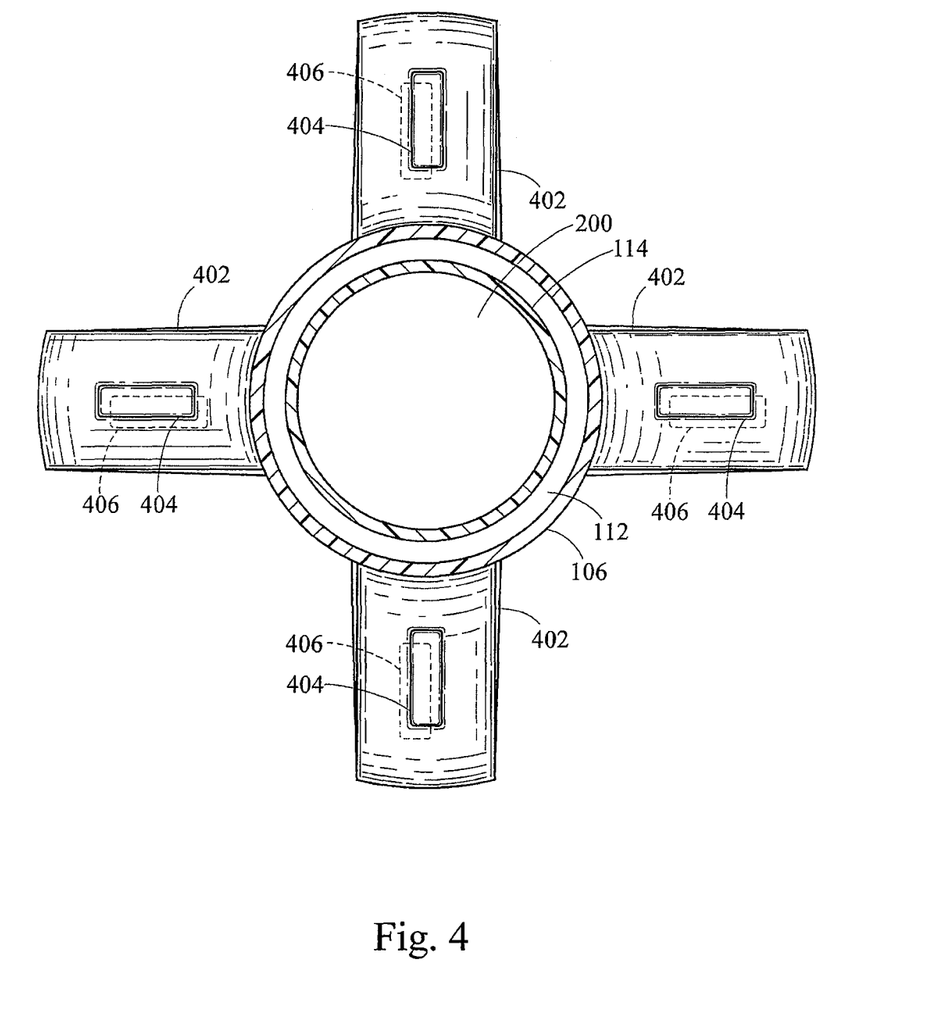
FIG. 4 is an illustration of a retention bolster taken along line 4-4 of FIG. 3.

Referring now to FIG. 3 and FIG. 4 (taken along line 4-4 of FIG. 3), the gastric port system 100 is illustrated implementing the first bolster 116 and a Malecot shaped second bolster 400. The bolster 116 is similar to that described above. The bolster 400 has a plurality of foldable members 402. In the embodiment illustrated, there is a magnet 404 disposed on each respective foldable member. There may be additional magnets on each foldable member 402 or there may be no magnets on some of the foldable members 402. Further, with reference to FIGS. 2 and 4, the magnets 404 are configured to be attracted to magnets 120, 202, 204, and 206 respectively. The foldable members 402 provide retention for the bolster 400 and are well suited to provide retention support for the gastric port system 100. A particular advantage to bolster 400 that may strengthen retention is that the bolster 400 may include additional magnets 406 which are designed to be attracted to magnets 404. In this configuration, magnets 404 may be disposed on the proximal side of foldable members 402 and magnets 406 may be disposed on the distal side of foldable members 402. The magnets 404 and 406 which are on opposing sides of each foldable member 402 will tend to retain the Malecot bolster 400 in the folded expanded configuration. Foldable members 402 may be collapsed to allow insertion of the bolster 400 through the stoma, and expanded to secure the port 106.

Figure 5:
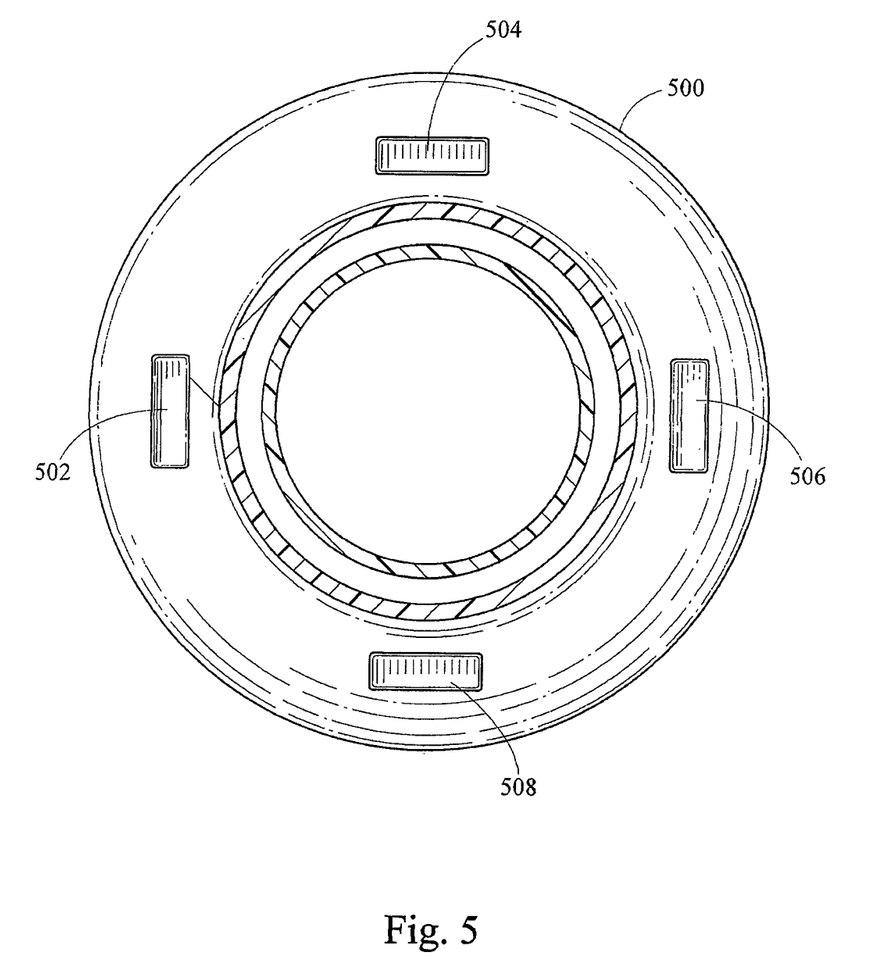
FIG. 5 is an illustration of a retention bolster for use in a gastric port system.

FIG. 5 illustrates another embodiment of the gastric port system 100 that may include a bolster 500 that may include pockets 502, 504, 506, and 508 that are configured to receive magnets (not shown). The pockets 502, 504, 506, and 508 may be stitched onto the surface of the bolster 500. Alternatively, the pockets 502, 504, 506, and 508 may be embedded within the bolster 500. The pockets 502, 504, 506, and 508 may be disposed on the bolster 500 such that magnets (not shown) may be inserted into one or more of the pockets 502, 504, 506, and 508. Depending on the application, each of the pockets 502, 504, 506, and 508 may be configured to receive one or more magnets. While four pockets are shown, it should be understood that any number of pockets may be disposed on bolster 500. For example, six pockets may be included and magnets may be inserted into each pocket, or two magnets may be inserted into three of the six pockets and so on. Further, the pockets 502, 504, 506, and 508 may be configured so that they may engage and retain magnets, such that the magnets are removable but will be retained within the pockets 502, 504, 506, and 508.

Figure 6:
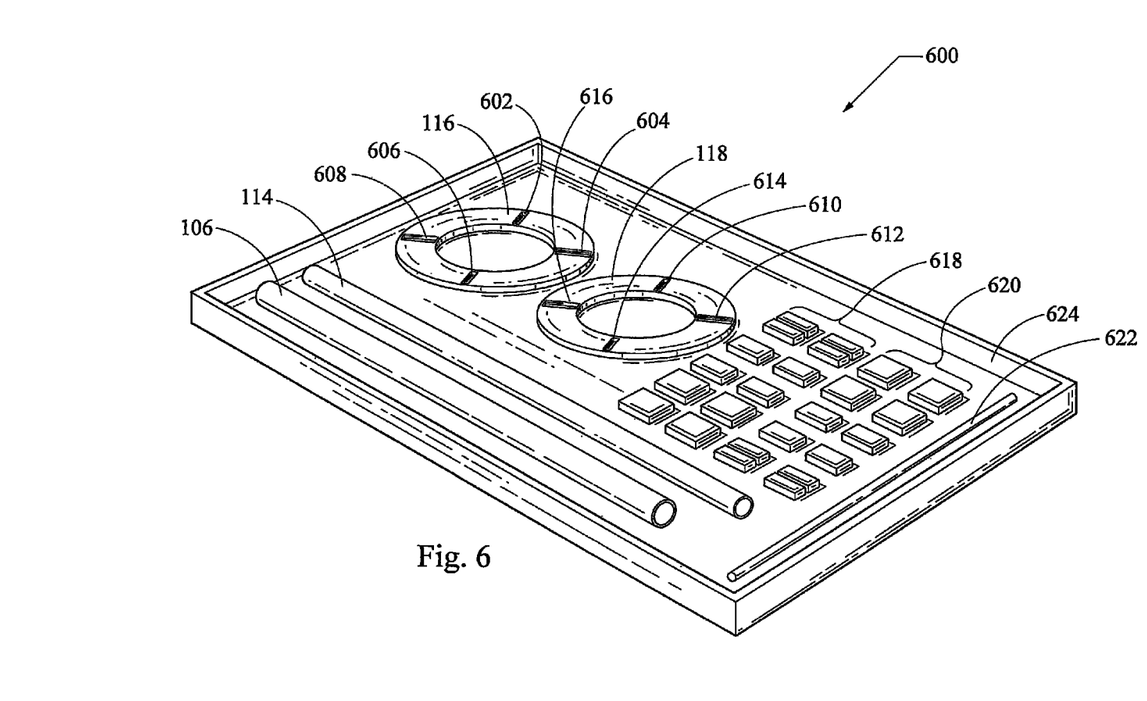
FIG. 6 is an illustration of a medical device kit that includes a gastric port system.

FIG. 6 illustrates a medical device kit 600 for use in the clinical environment. The kit 600 may include the port 106, the catheter 114, the first bolster 116 and the second bolster 118. Preferably, the first bolster 116 and the second bolster 118 include pockets 602, 604, 606, 608, 610, 612, 614, and 616 which are configured to receive magnets. The kit 600 may also include a first array 618 of magnets of varying sizes and magnetic strengths and a second array 620 of magnets of varying sizes and magnetic strengths. Generally, the magnets in the first array 618 are designed to be attracted to the magnets in the second array 620. However, certain magnets of the first array 618 may be attracted to each other. Likewise, certain magnets of the second array 620 may be attracted to each other. The kit 600 may also include a wire guide 622 and packaging 624.

It is therefore intended that the foregoing detailed description be regarded as illustrative rather than limiting, and that it be understood that it is the following claims, including all equivalents, that are intended to define the spirit and scope of this invention.

The invention claimed is:

1. A gastric port system for transport of materials to the interior of a body cavity comprising:
   a port configured to be disposed between a first body cavity and an area adjacent to the first body cavity; the port further comprising a distal portion, a proximal portion, and a passageway therethrough;
   a first non-inflatable bolster having an annular shape, the first bolster being disposed about the proximal portion of the port;
   wherein the proximal portion of the port extends proximally from the first bolster into the area adjacent to the first body cavity, the first bolster including at least one first magnet;
   a second non-inflatable bolster having an annular shape, the second bolster being disposed about the distal portion of the port;
   wherein the distal portion of the port extends distally from the second bolster into the first body cavity, the second bolster including at least one second magnet;
   wherein at least one of the first bolster and the second bolster is slidable relative to the port and the first and second bolsters contact respective bodily surfaces to define a thickness of tissue between the bolsters; and
   wherein the at least one first magnet is attracted to the at least one second magnet such that the first bolster and the second bolster are drawn together so that the at least one slidable bolster will adjust position to maintain contact with its respective bodily surface even if the thickness of the tissue between the bolsters decreases.

2. The gastric port system of claim 1 where the port is configured to extend through a bodily wall.

3. The gastric port system of claim 2 where the first bolster is configured to engage a first side of the bodily wall and the second bolster is configured to engage a second side of the bodily wall.

4. The gastric port system of claim 1 further comprising a catheter, with a lumen for the passage of materials, extending through at least a portion of the port.

5. The gastric port system of claim 1 where one of the first bolster and the second bolster is fixedly attached to the port.

6. The gastric port system of claim 1 where the first bolster is slidable relative to the proximal portion of the port and the second bolster is slidable relative to the distal portion of the port.

7. The gastric port system of claim 6, where the port further comprises a first retaining element for limiting axial movement of the first bolster and a second retaining element for limiting axial movement of the second bolster.

8. The gastric port system of claim 1 where the port further comprises a retaining element for limiting axial movement of one of the first bolster and the second bolster.

9. The gastric port system of claim 1 where the first body cavity is the abdominal cavity of the patient.

10. The gastric port system of claim 9 where the area adjacent to the first body cavity is external to the patient.

11. The gastric port system of claim 1 where the first body cavity is the abdominal cavity of the patient and the area adjacent to the first body cavity is the intestine of the patient.

12. A gastric port system for transport of materials to the interior of a body cavity comprising:
    a port configured to be disposed between a first body cavity and an area adjacent to the first body cavity; the port further comprising a distal portion, a proximal portion, and a passageway therethrough;
    a first non-inflatable bolster having an annular shape, the first non-inflatable bolster being disposed about the proximal portion of the port;
    wherein the proximal portion of the port extends proximally from the first bolster into the area adjacent to the first body cavity, the first non-inflatable bolster including at least one first pocket to receive at least one first magnet;
    a second non-inflatable bolster having an annular shape, the second non-inflatable bolster being disposed about the distal portion of the port;
    wherein the distal portion of the port extends distally from the second bolster into the first body cavity, the second non-inflatable bolster including at least one second pocket to receive at least one second magnet;
    wherein at least one of the first non-inflatable bolster and the second non-inflatable bolster is slidable relative to the port, and the first and second bolsters contact respective bodily surfaces to define a thickness of tissue between the bolsters; and
    wherein the at least one first magnet is attracted to the at least one second magnet such that the first non-inflatable bolster and the second non-inflatable bolster are drawn together so that the at least one slidable bolster will adjust position to maintain contact with its respective bodily surface, even if the thickness of the tissue between the bolsters decreases.

13. A gastric port system for transport of materials to the interior of a body cavity comprising:
    a port configured to be disposed between a first body cavity and an area adjacent to the first body cavity, the port further comprising a retaining element on a proximal portion of the port, a distal portion, and a passageway therethrough;
    a first non-inflatable bolster having an annular shape, the first bolster being disposed about the proximal portion of the port, the first bolster including at least one first magnet;
    a second non-inflatable bolster having an annular shape, the second bolster being disposed about the distal portion of the port, the second bolster including at least one second magnet;
    wherein the first bolster is slidable relative to the proximal portion of the port and the second bolster is slidable relative to the distal portion of the port and axial movement of the first bolster is limited by the retaining element, and the first and second bolsters contact respective bodily surfaces to define a thickness of tissue between the bolsters; and
    wherein the at least one first magnet is attracted to the at least one second magnet such that the first bolster and the second bolster are drawn together, so that the at least one slidable bolster will adjust position to maintain contact with its respective bodily surface even if the thickness of the tissue between the bolsters decreases.

* * * * *

UNITED STATES PATENT AND TRADEMARK OFFICE
CERTIFICATE OF CORRECTION

PATENT NO.        : 9,107,810 B2                                              Page 1 of 1
APPLICATION NO.   : 12/145148
DATED             : August 18, 2015
INVENTOR(S)       : F. Kristen Lyons

It is certified that error appears in the above-identified patent and that said Letters Patent is hereby corrected as shown below:

On the Title Page

Left column, item (12), replace "Bailey" with --Lyons--.

Left column, item (75), replace "Bailey, Bloomington, IN" with --Lyons, Ellettsville, IN--.

Signed and Sealed this
Twenty-first Day of June, 2016

Michelle K. Lee
*Director of the United States Patent and Trademark Office*